(12) United States Patent
Love

(10) Patent No.: US 7,208,000 B2
(45) Date of Patent: Apr. 24, 2007

(54) SURGICAL CUTTING DEVICE

(75) Inventor: Jack W. Love, Santa Barbara, CA (US)

(73) Assignee: Cardiomend, LLP, Santa Barbara, CA (US)

( * ) Notice: Subject to any disclaimer, the term of this patent is extended or adjusted under 35 U.S.C. 154(b) by 263 days.

(21) Appl. No.: 10/898,505

(22) Filed: Jul. 23, 2004

(65) Prior Publication Data

US 2006/0020280 A1   Jan. 26, 2006

(51) Int. Cl.
*A61B 17/32* (2006.01)
(52) U.S. Cl. .......................... 606/167; 83/586; 30/360
(58) Field of Classification Search ............... 606/166, 606/184, 185, 167, 45; 600/566, 567; 623/2.1, 623/2.11–2.19; 425/299, 295; 30/358, 360; 83/586
See application file for complete search history.

(56) References Cited

U.S. PATENT DOCUMENTS

| | | | |
|---|---|---|---|
| 2,255,846 A * | 9/1941 | Grammer | 83/582 |
| 4,056,854 A | 11/1977 | Boretos et al. | |
| 4,233,690 A | 11/1980 | Akins | |
| 4,309,929 A * | 1/1982 | Batson | 83/554 |
| 4,459,092 A * | 7/1984 | Hatakeyama | 425/112 |
| 4,858,317 A * | 8/1989 | Seib et al. | 30/115 |
| 5,142,973 A * | 9/1992 | Tur et al. | 99/538 |
| 5,163,953 A | 11/1992 | Vince | |
| 5,312,428 A * | 5/1994 | Lieberman | 606/166 |
| 5,332,402 A | 7/1994 | Teitelbaum | |
| 5,370,685 A | 12/1994 | Stevens | |
| 5,397,351 A | 3/1995 | Pavcnik et al. | |
| 5,411,552 A | 5/1995 | Anderson et al. | |

(Continued)

OTHER PUBLICATIONS

Moazami N, et al., Transluminal aoritc valve replacement. A feasibility study with a newly designed collapsible aortic valve., ASAIO, J. 1996;42:M381-5.

(Continued)

*Primary Examiner*—AnhTuan T. Nguyen
*Assistant Examiner*—Pavitra Kotini
(74) *Attorney, Agent, or Firm*—Bryan Cave LLP

(57) ABSTRACT

The present invention provides a single-use surgical cutting device for cutting a planar piece of tissue into a predetermined shape. The cutting device comprises a housing having one or more side walls, a top, a base, and a hollow interior portion. A blade retaining member is disposed within the housing between and substantially parallel to the top and base such that the blade retaining member can move vertically between the top and base. A blade defining a predetermined tissue shape is disposed on the bottom surface of the blade retaining member. A pressure mechanism creates potential energy for exerting a downward force on the top surface of the blade retaining member, such that when the blade retaining member is released, the pressure mechanism forces the blade retaining member downward with sufficient force to cut the piece of tissue. An actuator is configured to release the blade retaining member only once without disassembling the housing and resetting the pressure mechanism. Thus, a piece of tissue can be placed beneath the bottom surface of the blade retaining member on or parallel to the base and the actuating mechanism can be actuated to release the downward force on the blade retaining member to cut the piece of tissue into the desired shape, but the cutting device cannot readily be reused by an operator.

9 Claims, 14 Drawing Sheets

U.S. PATENT DOCUMENTS

| | | | |
|---|---|---|---|
| 5,449,384 A | 9/1995 | Johnson | |
| 5,464,417 A * | 11/1995 | Eick | 606/166 |
| 5,653,759 A | 8/1997 | Hogan et al. | |
| 5,716,399 A | 2/1998 | Love | |
| 6,033,419 A * | 3/2000 | Hamblin et al. | 606/184 |
| 6,120,534 A | 9/2000 | Ruiz | |
| 6,129,758 A | 10/2000 | Love | |
| 6,162,245 A | 12/2000 | Jayaraman | |
| 6,245,102 B1 | 6/2001 | Jayaraman | |
| 6,328,763 B1 * | 12/2001 | Love et al. | 623/2.15 |
| 6,406,493 B1 | 6/2002 | Tu et al. | |
| 6,425,902 B1 | 7/2002 | Love | |
| 6,458,153 B1 | 10/2002 | Bailey et al. | |
| 6,497,713 B1 * | 12/2002 | Tompkins et al. | 606/167 |
| 6,581,259 B1 * | 6/2003 | Yoshikawa et al. | 29/33 R |
| 6,598,307 B2 | 7/2003 | Love et al. | |
| 6,601,488 B1 * | 8/2003 | Muse et al. | 83/13 |
| 6,652,578 B2 | 11/2003 | Bailey et al. | |
| 6,676,698 B2 | 1/2004 | McGucking, Jr. et al. | |
| 6,678,962 B1 | 1/2004 | Love et al. | |
| 6,730,118 B2 | 5/2004 | Spenser et al. | |
| 6,932,937 B2 * | 8/2005 | Minami et al. | 264/511 |
| 2003/0191528 A1 | 10/2003 | Quijano et al. | |
| 2005/0075658 A1 * | 4/2005 | Duprat et al. | 606/166 |
| 2005/0229760 A1 * | 10/2005 | Chang | 83/437.1 |

OTHER PUBLICATIONS

Boudjemline Y, et al. Percutaneous aortic valve replacement: will we get there?, Heart 2001; 86:705-6.

Boudjemline Y, et al. Steps toward percutaneious aortic valve replacement. Circulation 2002;105(6):775-8.

Bonhoeffer P et al, Percutanous replacement of pulmonary valve in a right-ventricle to pulmonary-artery prosthetic conduit with valve dysfunction. Lancet 2000;356(9239):1403-5.

Love JW, Autologous pericardial reconstruction of semilunar valves. J Heart Valve Dis 1998;7:40-47.

Hanlon JG et al, Geometric optimization of a tissue pattern for semilunar valve reconstruction. J Heart Valve Dis 1999;8:609-613.

Hanlon JG et al, Pre-use intraoperative testing of autologous tissue for vavular surgery: a proof of concept study. J Heart Valve Dis 1999;8:614-624.

Hanlon JG et al, Advances in semilunar valve reconstruction. CVE 2001;6:1-4.

Magovern GJ et al, Sutureless Prosthetic Heart Valves, J. Thoracic and Cardiovascular Surgery 1963; 46:726-736.

* cited by examiner

SURGICAL CUTTING DEVICE

FIELD OF THE INVENTION

The present invention relates generally to surgical cutting instruments. More particularly, the present invention pertains to a sterilzable single-use surgical cutting device for cutting a planar piece of tissue into a predetermined shape.

BACKGROUND OF THE INVENTION

To overcome disadvantages of the prior methods of valve reconstruction, Cardiomend LLC (the assignee of the present application), has developed improved, more easily reproducible, less complicated, and generally standardized, methods and devices for reconstructing heart valves. These methods and devices are generally described in Love U.S. Pat. No. 5,716,399, Love U.S. Pat. No. 6,129,758, Love et al U.S. Pat. No. 6,328,763, Love U.S. Pat. No. 6,425,902, Love et al. U.S. Pat. No. 6,598,307, and Love et al. U.S. Pat. No. 6,678,962 (the "Love Patents"), each of which is incorporated herein by reference in its entirety. The Love Patents generally describe innovative methods and devices for reconstructing semilunar valves (aortic and pulmonic) using a novel unitary trefoil tissue pattern, which is preferably made of lightly tanned autologous pericardium. The methods described in the Love Patents generally include the steps of (a) removing the diseased native valve leaflets, (b) sizing of the heart valve based on the distance between adjacent commissures of the native valve annulus, (c) cutting a trefoil tissue pattern corresponding in size to the native valve annulus, (d) temporarily mounting the tissue pattern on a surgical instrument for holding the tissue in a configuration of a circulatory system valve to facilitate attachment of the tissue, and (e) suturing the tissue to the native valve annulus.

Prior art FIG. 1 illustrates an embodiment of a trefoil tissue pattern for use with the methods and devices disclosed in the Love Patents. The tissue pattern is more fully described and shown in Love et al. U.S. Pat. No. 6,425,902. The trefoil pattern is used to form a tri-leaflet valve structure. An embodiment of the trefoil valve tissue pattern 25 has three lobes, 16a, 16b and 16c, arranged about a center orifice 19. Each of lobes 16a, 16b and 16c of the trefoil valve tissue pattern, when oriented in the configuration of a valve and affixed to the native valve annulus, will form one leaflet or lobe of the valve structure. The tissue pattern is preferably cut in a predetermined size that corresponds to the size of the native valve annulus.

The present invention relates to a device for cutting a tissue pattern for use with the methods described in the Love Patents and, in particular, for use in connection with the stent and method for repairing or replacing a circulatory system valve as described in co-pending, commonly assigned U.S. patent application Ser. No. 10/898,703, entitled Stent and Method for Circulatory System Valve Repair or Replacement, filed concurrently herewith and incorporated herein by reference in its entirety. Among the advantages of the present invention is that it provides a mechanism for quickly and easily cutting a precise tissue pattern without dragging the material and possibly tearing the tissue or distorting the geometry of the tissue pattern, as would often occur using a straight scalpel blade. The cutting device can also quickly attach a stent to the valve repair material. Furthermore, the cutting device cannot readily be re-used so as to avoid the risk of contamination, infection, and ineffective cutting resulting from the re-use of the cutting blade.

SUMMARY OF THE INVENTION

The present invention provides a sterilizable single-use surgical cutting device for cutting a planar piece of tissue into a predetermined shape. The cutting device comprises a housing having one or more side walls, a top, a base, and a hollow interior portion. A blade retaining member is disposed within the housing between the top and base. The blade retaining member has a top surface and a bottom surface having a blade disposed thereon, which defines the predetermined tissue shape. In one embodiment, the predetermined shape comprises a trefoil shape optimized for cutting tissue to be used for repair or reconstruction of a semilunar heart valve. The top surface and bottom surface of the bade retaining member are substantially parallel to the top and the base of the housing. The blade retaining member moves vertically between the top and base. A pressure mechanism creates potential energy for exerting a downward force on the top surface of the blade retaining member. When the blade retaining member is released, the pressure mechanism forces the blade retaining member downward with sufficient force to cut the piece of tissue. An actuator is configured to release the blade retaining member upon actuation only once without disassembling the housing and resetting the pressure mechanism. Thus, a piece of tissue can be placed beneath the bottom surface of the blade retaining member on or parallel to the base and the actuating mechanism can be actuated to release the downward force on the blade retaining member to cut the piece of tissue into the predetermined shape, but the cutting device cannot readily be reused by an operator.

The housing is preferably sized such that the cutting device is portable and essentially hand-sized, so that the device can conveniently be used in an operating room during a surgical procedure. The housing is preferably constructed such that it cannot easily be disassembled by the operator. Thus, the operator is prevented from easily resetting the pressure mechanism and reusing the cutting device.

In one embodiment, the pressure mechanism comprises one or more springs compressed between the top of the housing and the blade retaining member and the actuating mechanism comprises a mechanism for releasing the compressed springs.

For example, the device can comprise three springs distributed around the blade retaining member at a substantially equal separation, whereby the downward force exerted by the springs is equally distributed around the blade retaining member.

The actuator can comprise a cylindrical shaft passing through a center hole in the housing. A knob attached to the top end of the shaft rests on the top of the housing for rotating the shaft about its axis. One or more horizontal projections from the bottom end of the shaft project from the shaft orthogonal to the axis of the shaft. The blade retaining member comprises a center opening having a profile that allows the bottom end of the cylindrical shaft and projections to pass through the blade retaining member only when aligned with the center opening. The cutting device can be placed in a ready position by passing the bottom end of the shaft and projections through the center opening of the blade retaining member, pressing the blade retaining member upward against the top of the housing to compress the springs, rotating the shaft such that the pins are not aligned with the center opening of the blade retaining member so as to retain the blade retaining member against the housing with the springs in a compressed condition. The cutting device is actuated from the ready position by turning the knob to a cut position where the projections are aligned with the center opening of the blade retaining member so as to allow the projections and bottom end of the shaft to pass through the center opening of the blade retaining member and release the blade retaining member, allowing the springs to decompress and force the blade retaining member downward.

The cutting device can include a tissue holding plate. In this embodiment, the housing preferably comprises a slot in a side wall near the base for receiving the tissue holding plate and retaining it below the blade retaining member during cutting. The tissue holding plate preferably has a slot in its top surface for receiving a stent to be attached to the tissue. When inserted into the slot, the stent is flush with the top surface of the tissue holding plate. The tissue holding plate can have a lower base plate and an upper tissue retaining plate removably configured to be positioned on and attached to the lower base plate. The upper tissue retaining plate preferably has an opening therein for allowing the blades to pass through. Thus, the tissue can be held on the tissue holding plate by sandwiching the tissue between the lower base plate and upper tissue retaining plate. Retaining tabs on the lower base plate can be used to secure the upper tissue retaining place to the lower base plate. The housing can include a planar base plate below the tissue holding plate. The device preferably also includes a mechanism for raising the blade retaining member after the tissue has been cut to allow the tissue and holding plate to be removed from the housing.

BRIEF DESCRIPTION OF THE DRAWINGS

These and other features, aspects and advantages of the invention will become more fully apparent from the following detailed description, appended claims, and accompanying drawings where:

Figure 1:
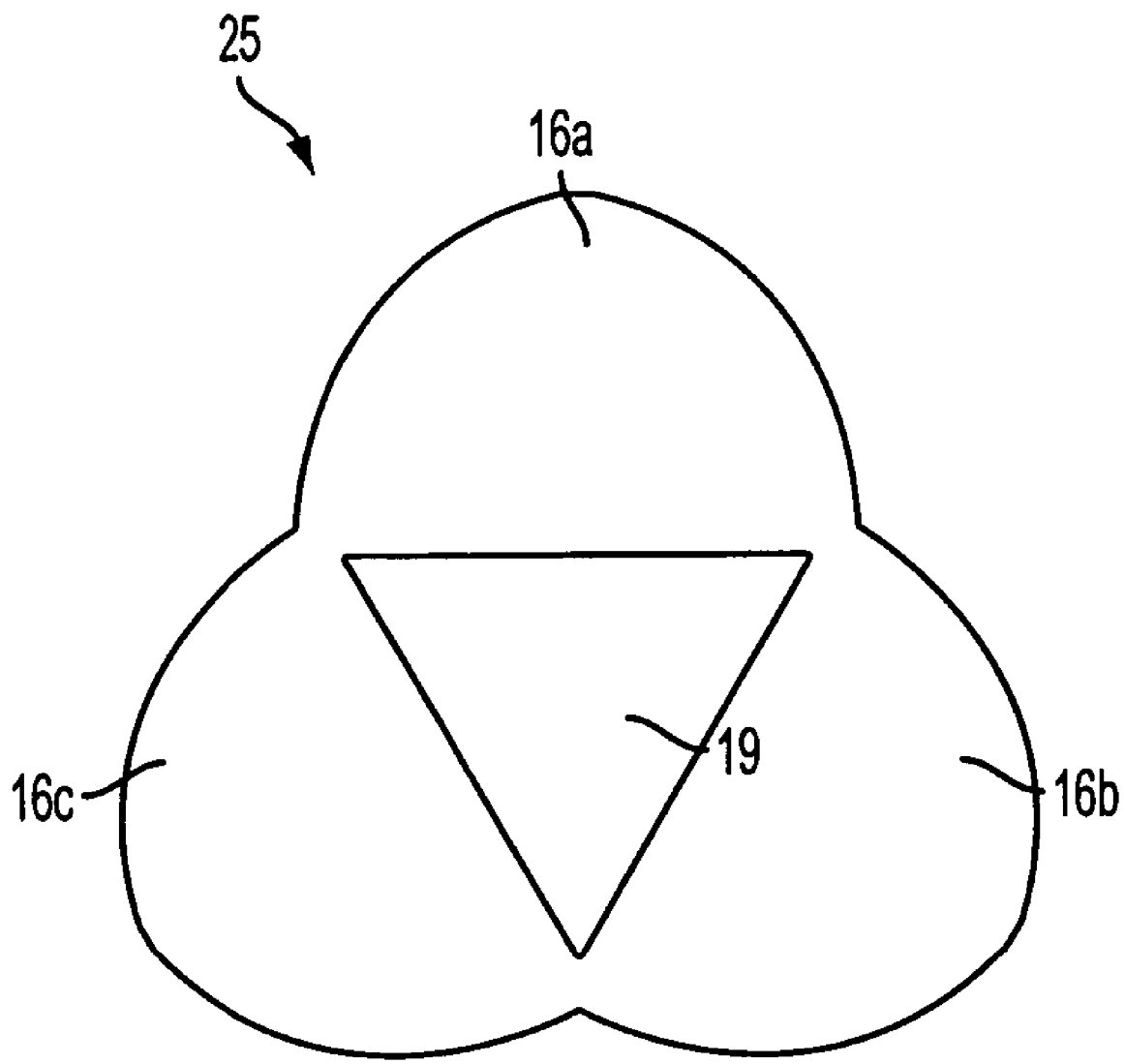
FIG. 1 illustrates an embodiment of a trefoil tissue pattern for use with the invention.

For clarity, the drawing figures illustrate the general configuration of a preferred embodiment of the device. Descriptions and details of well-known features and alternative embodiments of the invention are omitted to avoid unnecessarily obscuring the invention and because people of ordinary skill in the art will appreciate and understand the invention is capable of and teaches various alternative embodiments. The drawings are provided for illustrative purposes only and should not be used to unduly limit the scope of the invention.

DETAILED DESCRIPTION OF THE INVENTION

The present invention provides a sterilizable single-use surgical cutting device for cutting a planar piece of tissue into a predetermined shape.

Figure 2A:
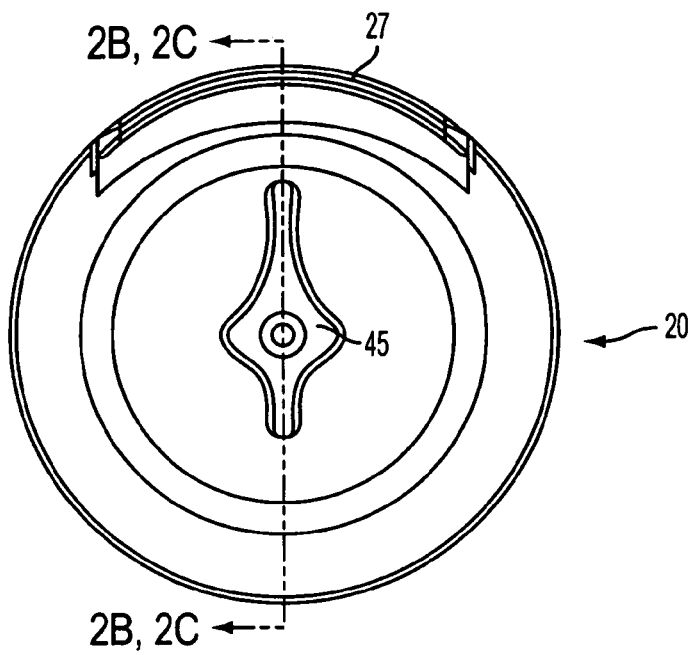
FIG. 2A illustrates a top view of a cutting device.
Figure 2B:
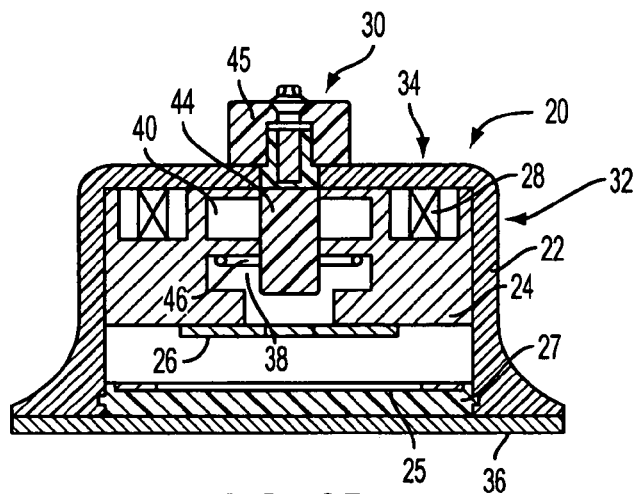
FIG. 2B illustrates a cross-sectional front view of a cutting device with the blade retaining member raised in a ready position.

With reference to FIGS. 2A and 2B, the cutting device 20 generally comprises a housing 22, which contains a blade retaining member 24 having a die blade 26 in the shape of the preferred tissue pattern affixed to the bottom. An uncut piece of tissue 25 is harvested and placed on a tissue holding plate 27 beneath the blade 26. In its initial ready position, a pressure mechanism, such as compressed springs 28, create potential energy for exerting a downward force on the top surface of the blade retaining member 24. The cutting action is triggered by turning actuator 30 to release the blade retaining member 24, and allow springs 28 to force the blade retaining member 24 downward with sufficient force to cut the piece of tissue 25 into the desired shape.

Figure 3:
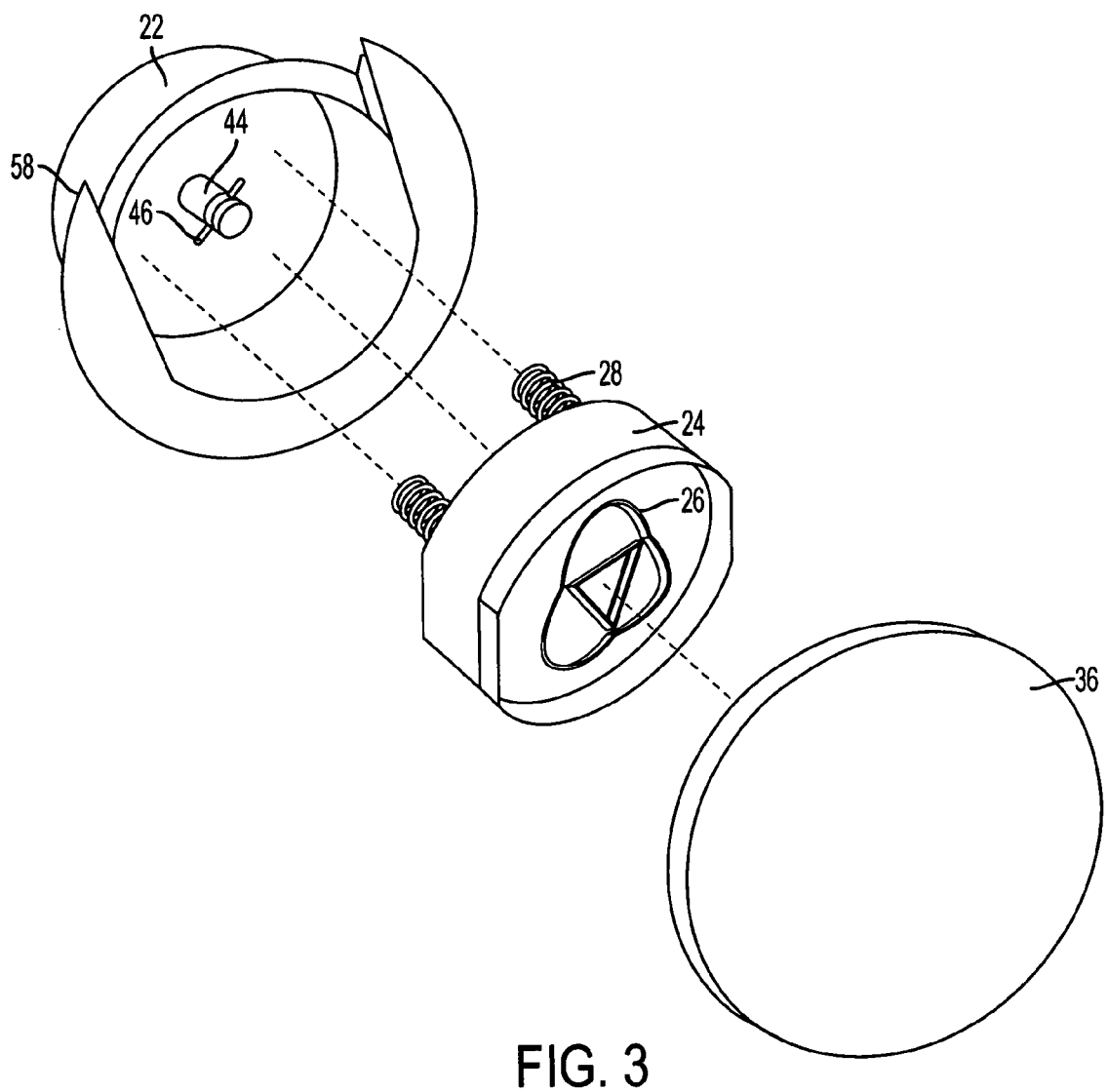
FIG. 3 illustrates an exploded bottom view of a cutting device.

The housing 22 is preferably cylindrical in shape, but can be any of a variety of shapes. It can be made from any of a variety of materials, such as plastic or metal. As shown in FIGS. 2A and 3, the housing 22 preferably comprises a substantially cylindrical side wall portion 32 and a top 34. A base 36 is preferably securely affixed to the upper housing 22 by a permanent or semi-permanent means such as rivets or bonding so as to prevent the operator from disassembling the cutting device to reset the cutting mechanism to reuse the device. The housing defines a hollow interior portion for containing the cutting mechanism.

Figure 4:
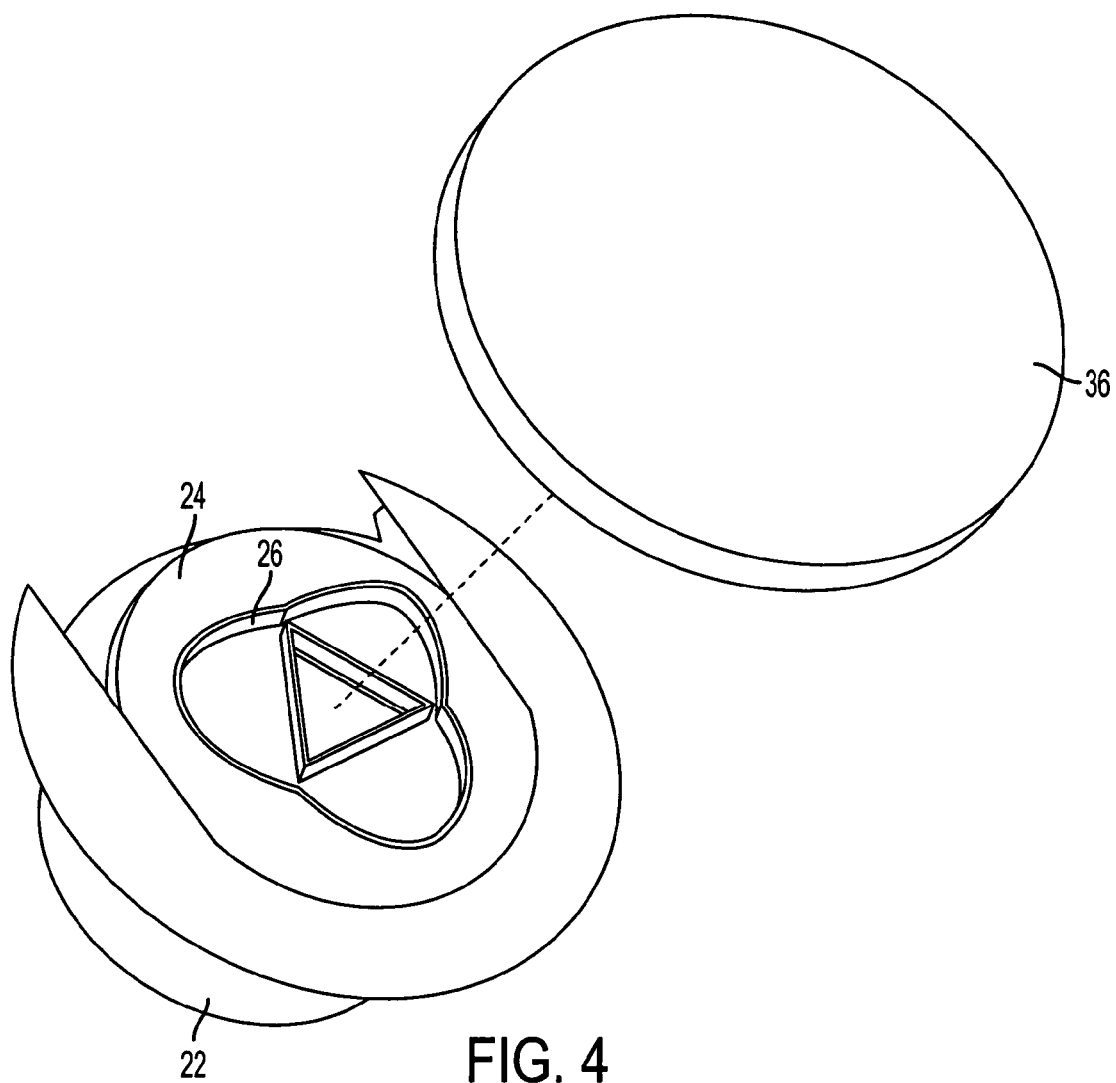
FIG. 4 illustrates a illustrates a bottom view of a cutting device with the base removed.

Blade retaining member 24 fits concentrically within housing 22 such that it can slide up and down along the side wall portion 32 of the housing. In the illustrated embodiment, the blade retaining member 24 is a piston-like cylindrical member fitting closely within a cylindrical housing 22 such that the blade retaining member is guided up and down by the wall of the housing. As shown in FIGS. 3 and 4, a blade 26 is affixed to the bottom of blade retaining member 24. Blade 26 is preferably a razor-sharpened metal blade precisely configured to conform to the outline of all or part of the desired tissue pattern. In the illustrated embodiment, the blade is configured to cut tissue in a trefoil pattern to form a heart valve repair or replacement structure as is fully described in Love U.S. Pat. No. 6,328,763, incorporated herein by reference. The blade can be embedded in blade retaining member 24 made of biocompatible material such as thermoplastic, TEFLON, polycarbonate, polysulfone, or metal such as stainless steel or aluminum.

Figure 5:
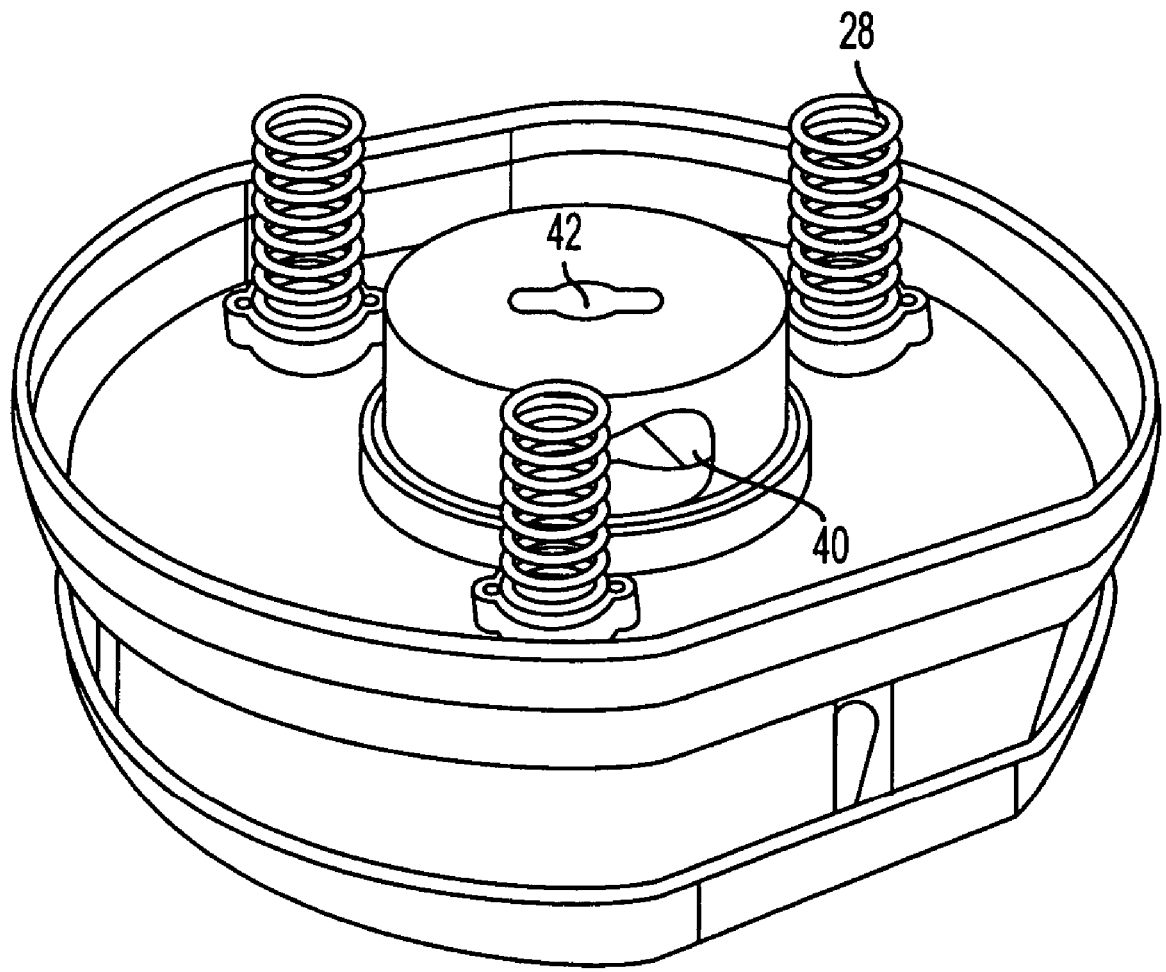
FIG. 5 illustrates a top view of a blade retaining member.
Figure 6:
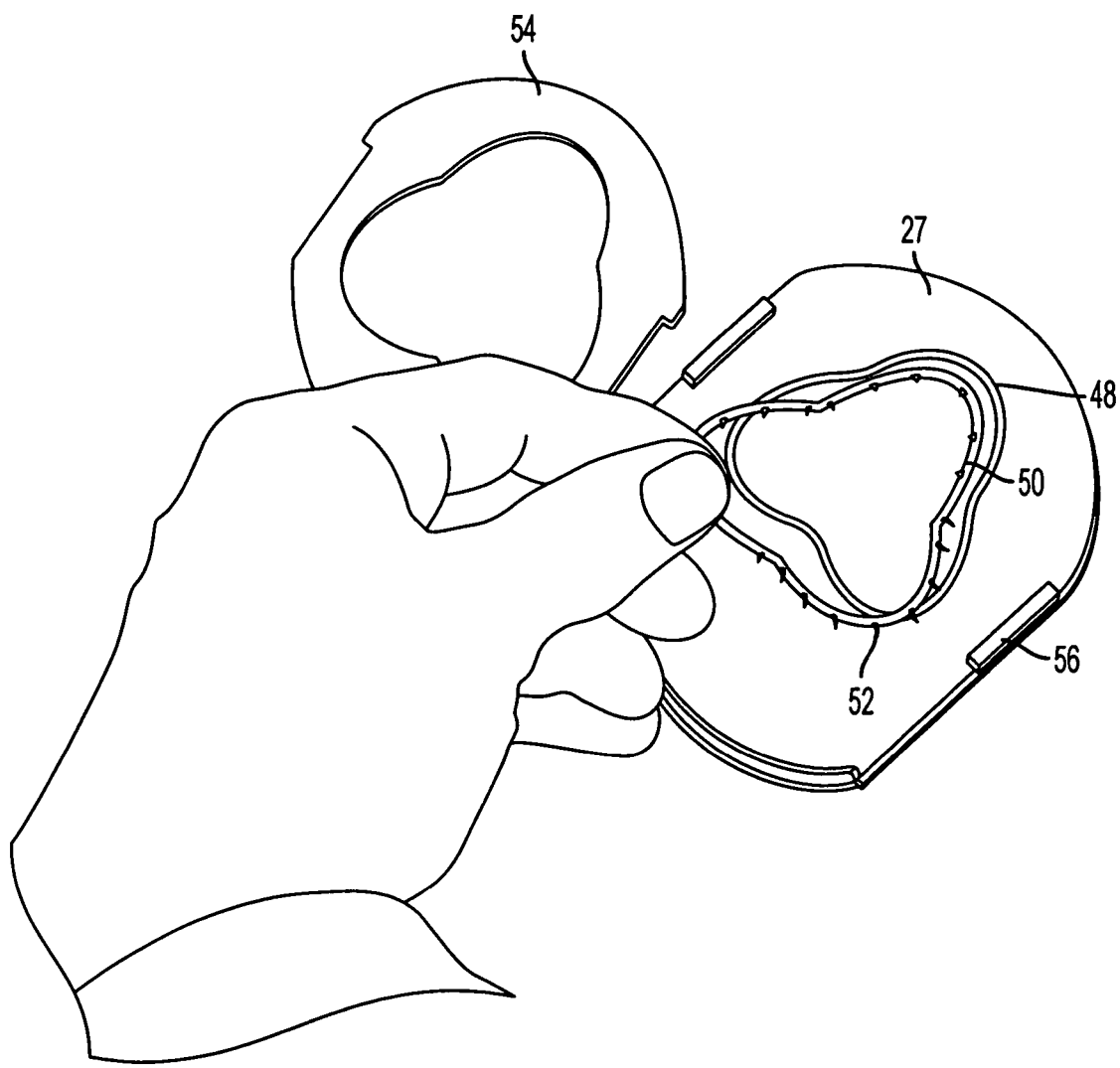
FIGS. 6–9 illustrate a tissue holding plate.

In the illustrated embodiment, blade retaining member 24 cooperates with actuator 30 and springs 28 to trigger a cutting action. In this embodiment, the blade retaining member 24 comprises a lower slot 38 and an upper slot 40 and a center opening 42 having a cylindrical center portion for receiving a cylindrical shaft. Actuator 30 comprises a vertical cylindrical shaft 44 and two horizontal pins 46 projecting from the bottom end of the shaft orthogonal to the axis of the shaft. The shaft 44 fits within a cylindrical opening in the top 34 of the housing. Actuator 30 includes a knob 45 attached to the upper end of shaft 44 and resting on the outer surface of the top 34 of the housing. Knob 45 is used to rotate shaft 44 about its vertical axis. As can be seen in FIG. 5, center opening 42 of the blade retaining member 24 has a profile that allows the bottom end of the cylindrical shaft 44 and pins 46 to be inserted into the opening 42 and passed through the center of the blade retaining member 24 when the pins 46 are aligned with the profile of center opening 42. When pins 46 are not aligned with the profile of the center opening 42, they prevent the blade retaining member 24 from sliding vertically along the shaft 44.

FIG. 2B illustrates the device in its initial ready position. The cutting device is placed in the ready position by passing the bottom end of the shaft 44 and pins 46 through the center opening 42 of the blade retaining member 24, pressing the blade retaining member 24 upward against the top surface 34 of the housing to compress the springs 28. The blade retaining member 24 is pushed up against the top 34 of the housing to a position where the pins 46 are aligned with lower slot 38. The shaft 44 is then rotated relative to the opening 42, such that the pins 46 rotate within lower slot 38 and are no longer aligned with the profile of the center opening 42. With the pins not aligned with opening 42, the blade retaining member 24 is unable to move downward. Thus, the blade retaining member 24 is retained against the top 34 of the housing with the springs 28 compressed between the blade retaining member 24 and the top 34 of the housing. In the ready position, the blade retaining member 24 is raised to its highest position with the springs 28 compressed to provide potential energy so that when the blade retaining member 24 is released, it will be forced downward against the piece of tissue 25 with sufficient force to cut the tissue. The device is preferably delivered to the operator in the ready position with the base 36 of the housing attached by rivets, bounding or other permanent or semi-permanent means.

Figure 2C:
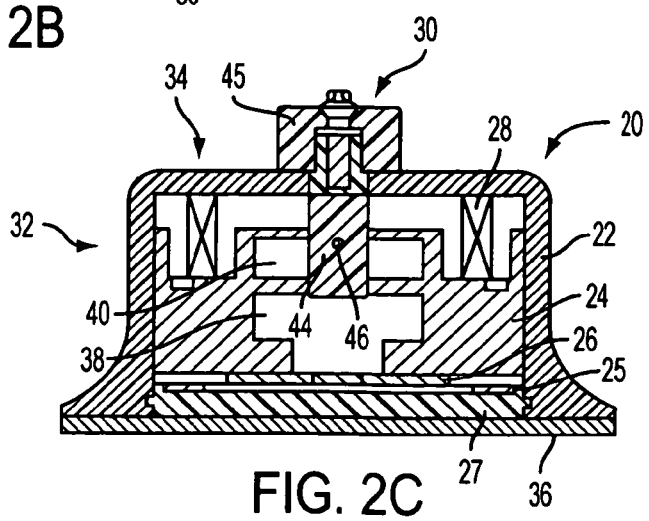
FIG. 2C illustrates a cross-sectional front view of a cutting device with the blade retaining member lowered in a cutting position.

FIG. 2C illustrates the device with the blade retaining member 24 released and in the cutting position. The blade retaining member 24 is released by turning the knob 45 to rotate the shaft 44 of the actuator 30. In the cutting position, the pins 46 are aligned with the center opening 42 of the blade retaining member so as to allow the pins to pass through the center opening 42 and release the blade retaining member. The springs 28 are thus allowed to decompress and force the blade retaining member downward causing the blade 26 to cut the tissue. As shown in FIG. 2C, the blade retaining member 24 is in its lowest position with the blades against the tissue 25.

When the blade retaining member 24 is in the cutting position, the pins 46 are aligned with the upper slot 40. The upper slot 40 cooperates with the actuator 30 to raise the blade retaining member 24 slightly so that the cut tissue 25 can be removed from the cutting device 20. As shown in FIG. 5, the upper slot 40 has a sloped top surface. When the pins 46 are inserted into the upper slot 40, the sloped upper surface of upper slot 40 rests against the pins. When the actuator is turned, the rotation of the pins 46 against the sloped upper surface of the upper slot 40 causes the blade retaining member 24 to raise slightly so that blade 26 is no longer in contact with tissue 25, allowing the tissue to be removed from the device.

In the illustrated embodiment, the pressure mechanism comprises three springs 28 distributed at 120 degree or other intervals about the blade retaining member so as to equally distribute the downward force equally on the blade retaining member. However, any of a wide variety of pressure mechanisms that creates a potential energy for forcing the blade retaining member downward can be used. For example, an electric actuator or compressed gas mechanism could be used.

Figure 7:
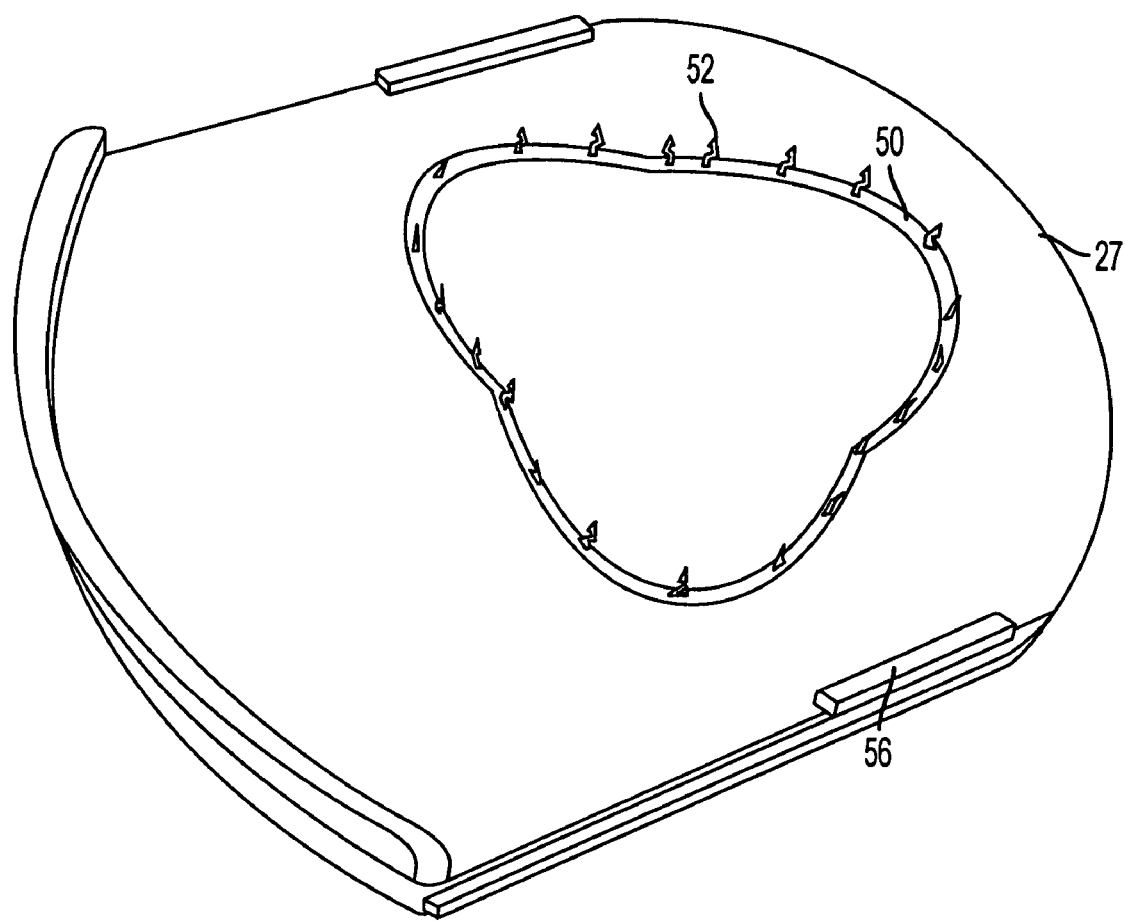
Figure 8:
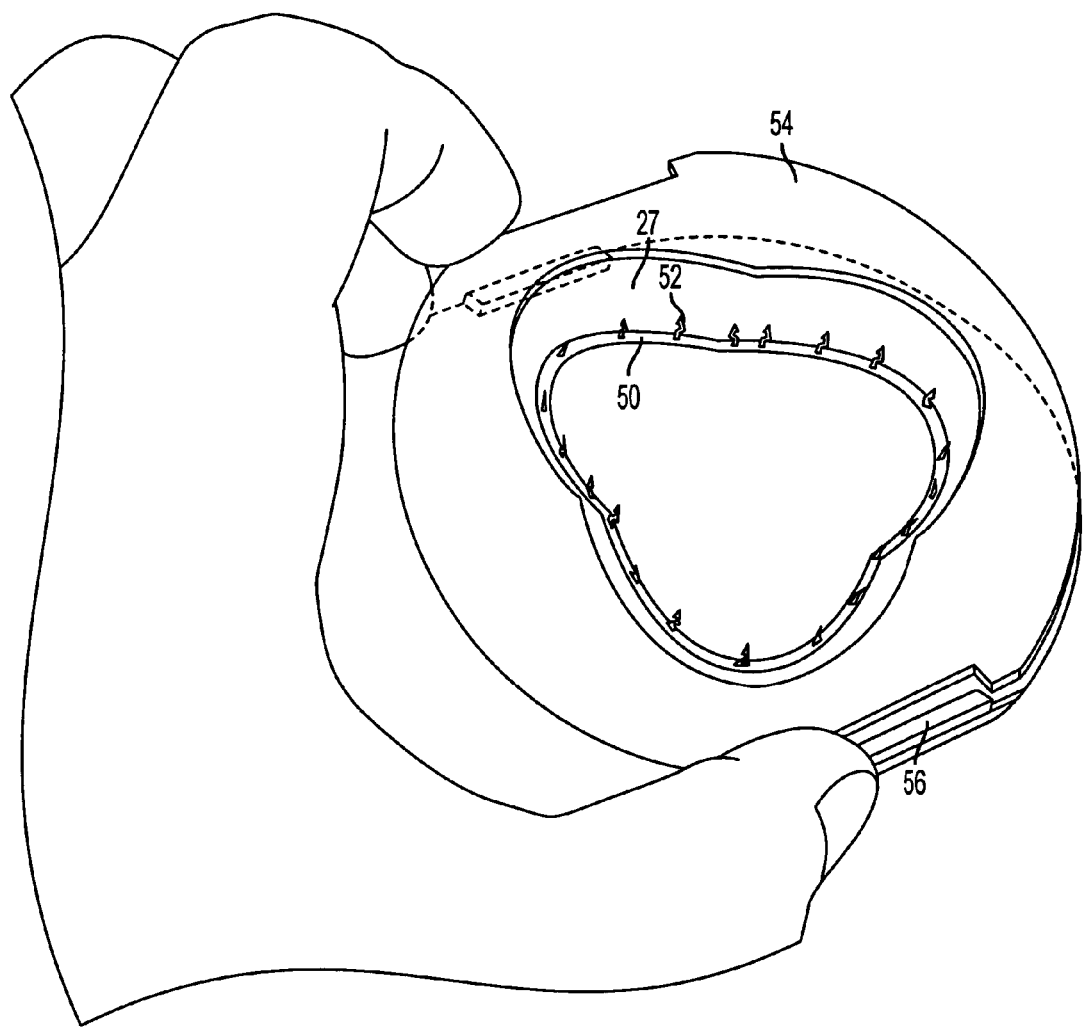
Figure 9:
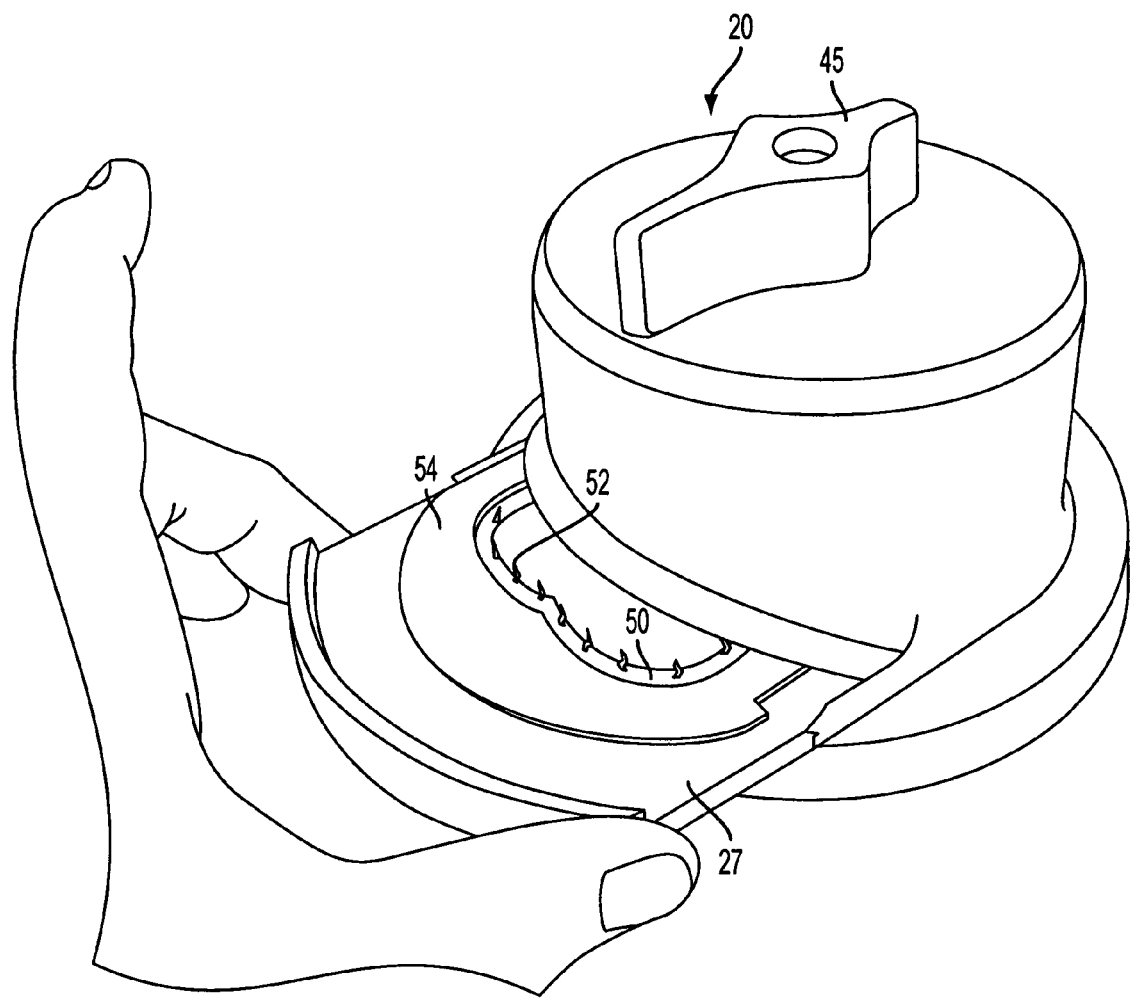
Figure 10:
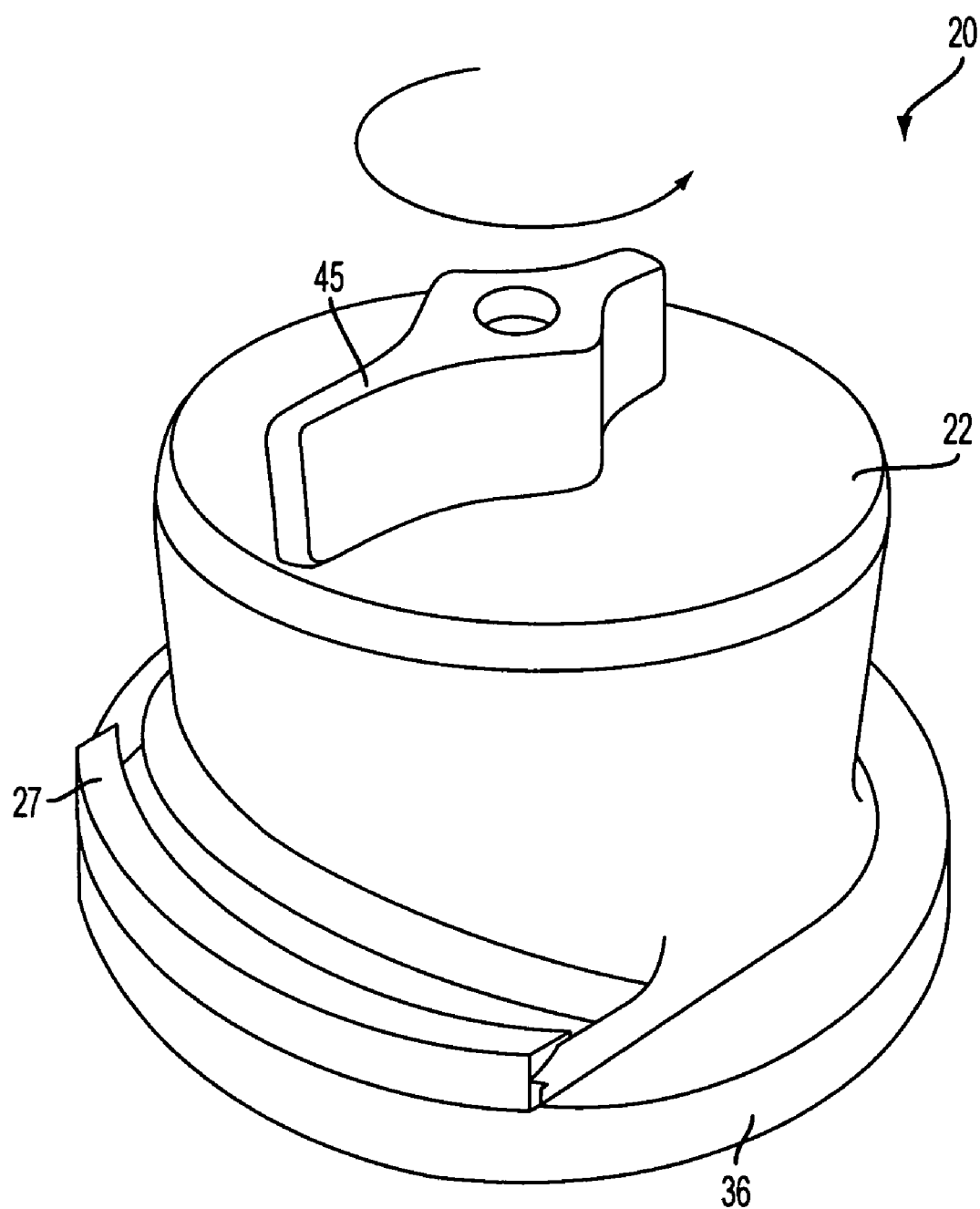
FIG. 10 illustrates the device with the tissue holding plate installed.

FIGS. 6–10 illustrate an embodiment of a preferred tissue holding plate 27. The tissue holding plate 27 is preferably made of a biocompatible material such as thermoplastic. The plate preferably comprises a slot 48 for receiving a trefoil shaped stent 50, which is fully described in co-pending a application Ser. No. 10/898,703, incorporated herein by reference. The stent 50 corresponds in shape and size to blade 26. Stent 50 preferably fits within slot 48 such that it is flush with or slightly raised from the surface of holding plate 27 as shown in FIG. 7. Stent 50 preferably comprises a plurality of piercing members such as barbs 52, which project from the surface of the stent 50 above the plane of the holding plate 27. The tissue holding plate 27 can also include a retaining plate 54. After the stent is placed in the slot 48, the uncut piece of tissue is laid on top of the stent. As shown in FIG. 8, the tissue retaining plate 54 is then placed on top of the tissue piece so as to force barbs 52 through the tissue. Tissue holding plate 27 is secured in place using tabs 56. Once the tissue is secured on the tissue holding plate 27, the holding plate 27 can be inserted into the cutting device through a slot 58 in the side wall 32 so that the holding plate 27 rests on base 36. As illustrated in FIG. 10, once the tissue and stent have been secured to the holding plate and the plate inserted into the cutting device, the actuator knob 45 is turned to cut the tissue.

Figure 11A:
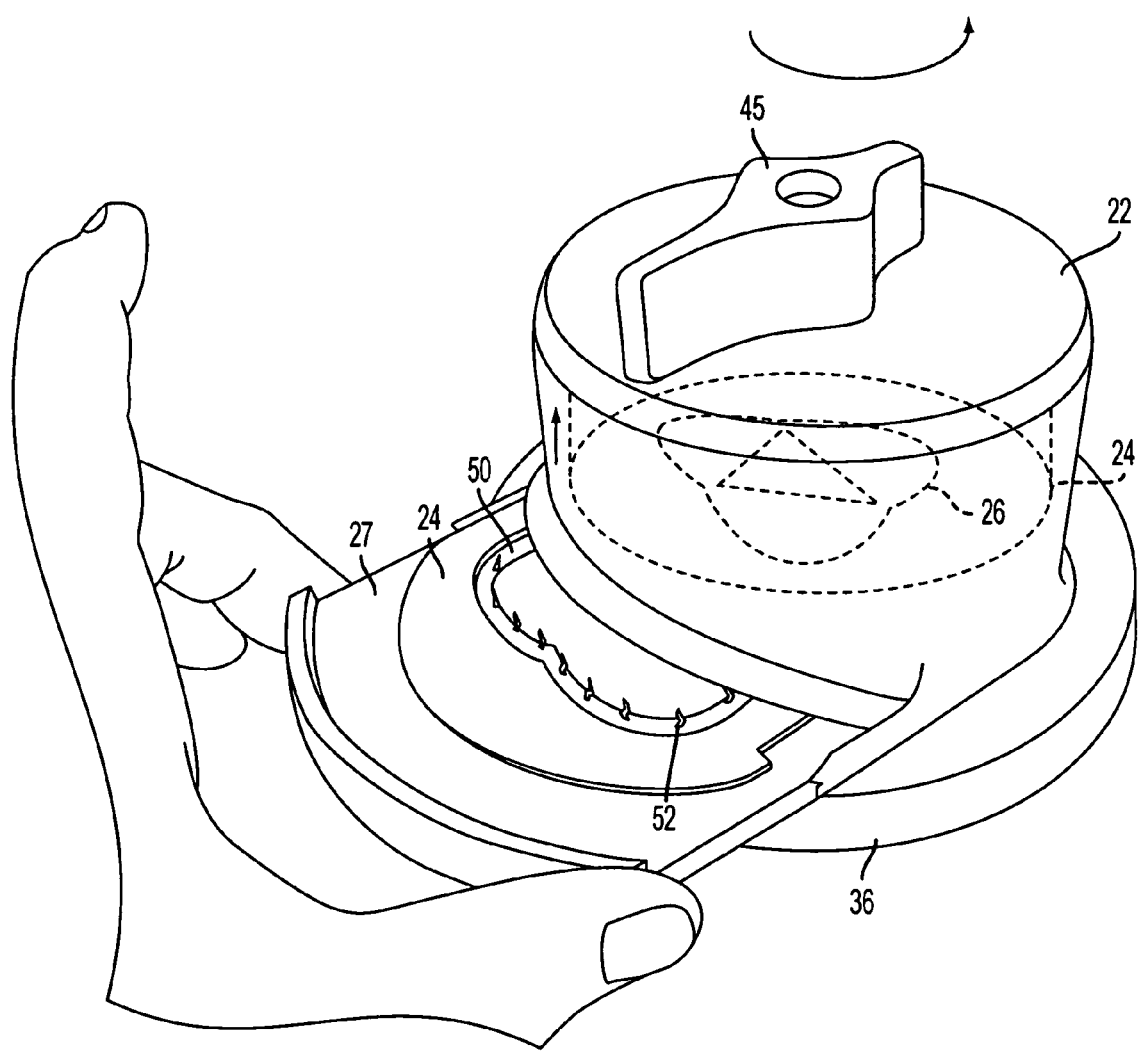
FIG. 11A–11C illustrate the movement of the tissue blade retaining member within the device.
Figure 11B:
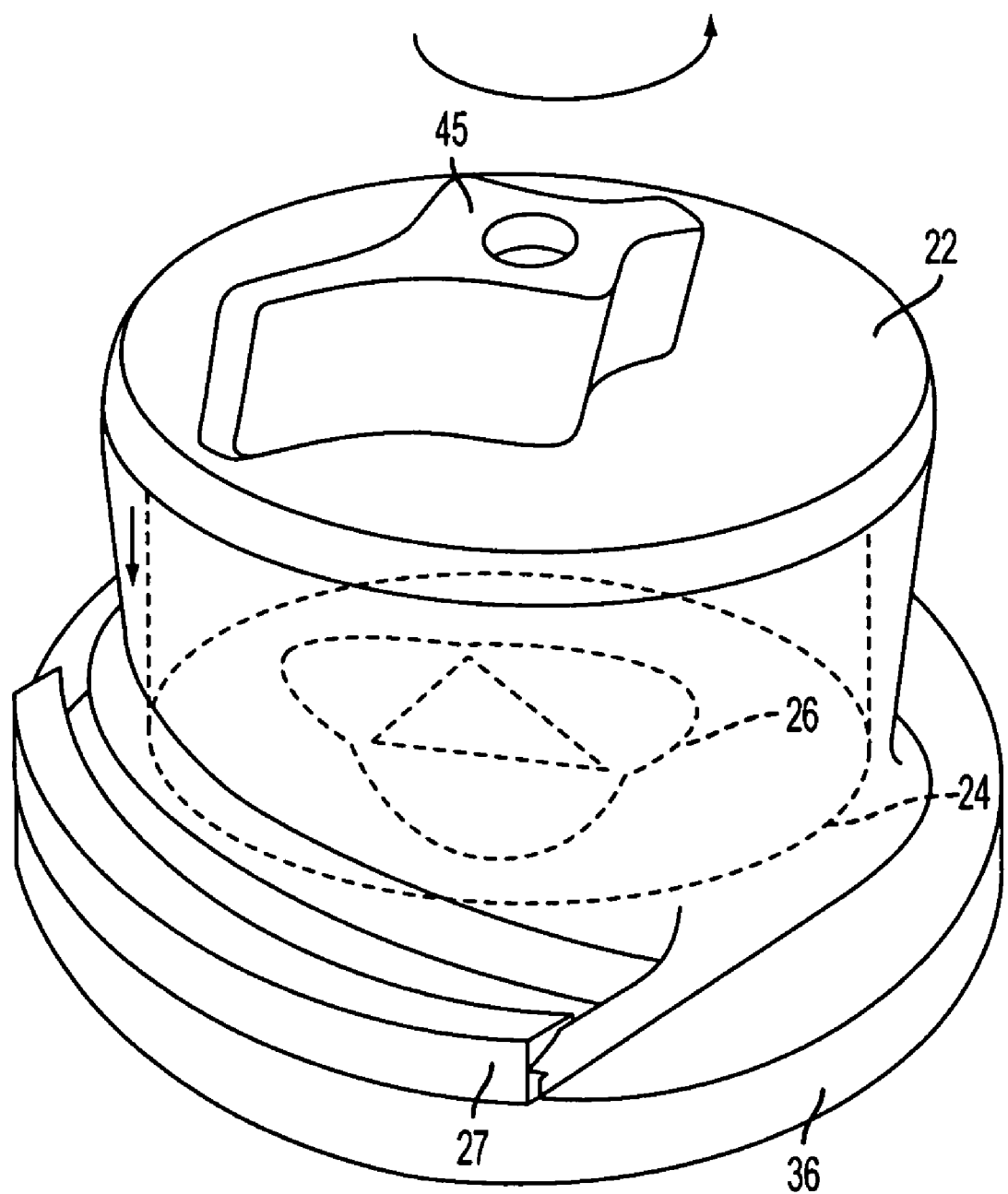
Figure 11C:
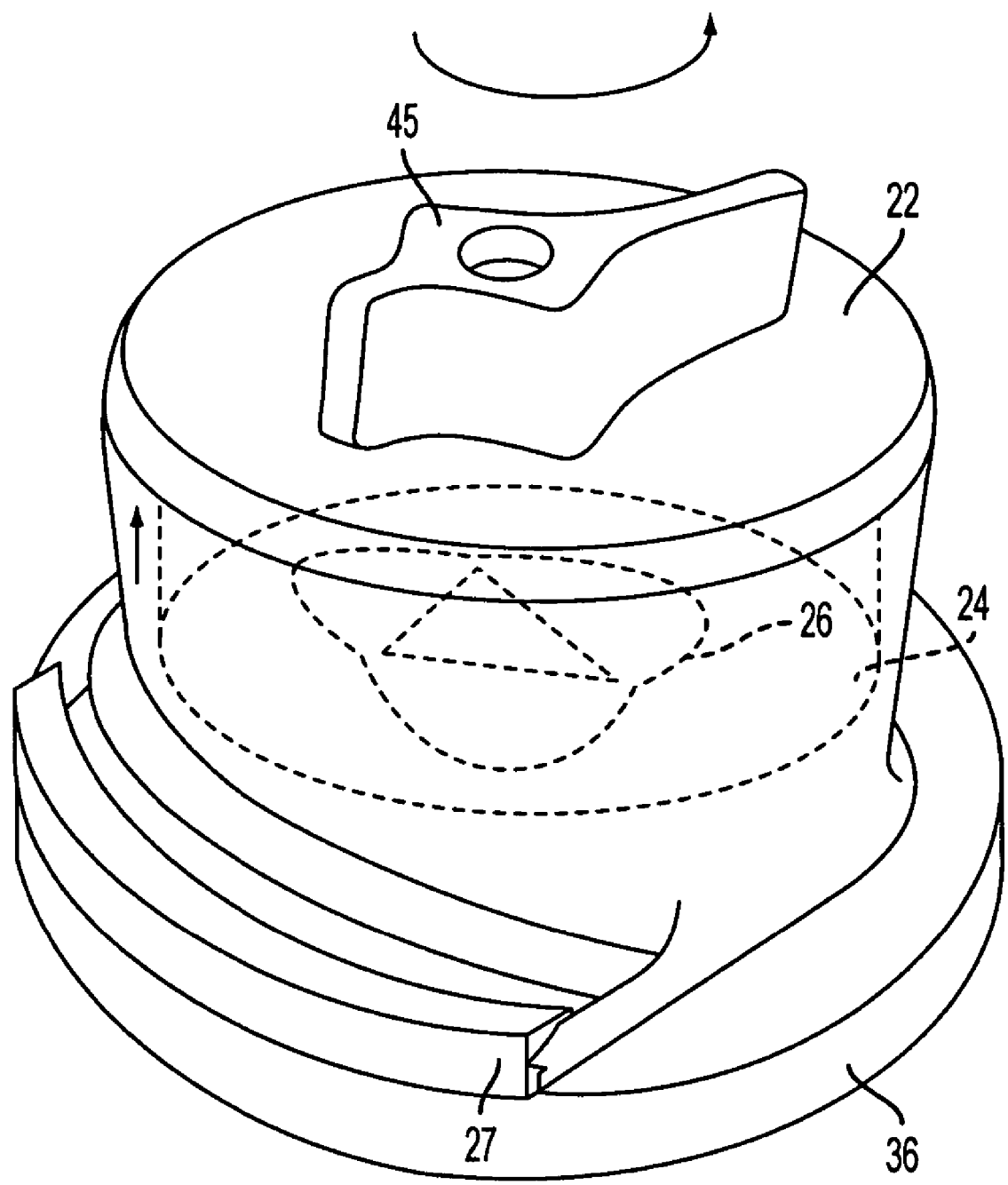

FIGS. 11A–C illustrate the movement of the blade retaining member 24 during operation. FIG. 11A illustrates the device in the ready position with the blade retaining member 24 raised to allow the tissue holding plate 27 to be inserted in slot 58 and positioned below the blade 26. Knob 45 is then rotated to turn actuator shaft 44 allowing the blade retaining member 24 to be released and forced downward by springs 48 (FIG. 5) with sufficient force to cut the tissue. FIG. 11B illustrates the blade retaining member 24 in a cutting position, with the blade retaining member in a lowered position resting against the tissue holding plate 27. In order to remove the holding plate 27 from the device, it is necessary to raise the blade retaining member 24 slightly so that the blade 26 is no longer in contact with the tissue. As illustrated in 11C, the blade retaining member 24 can be raised slightly by turning the knob of the actuator to an open position. As discussed above, the blade retaining member 24 is raised by cooperation of the actuator with the upper slot 40 of the blade retaining member 24 (FIG. 2C).

Figure 12:
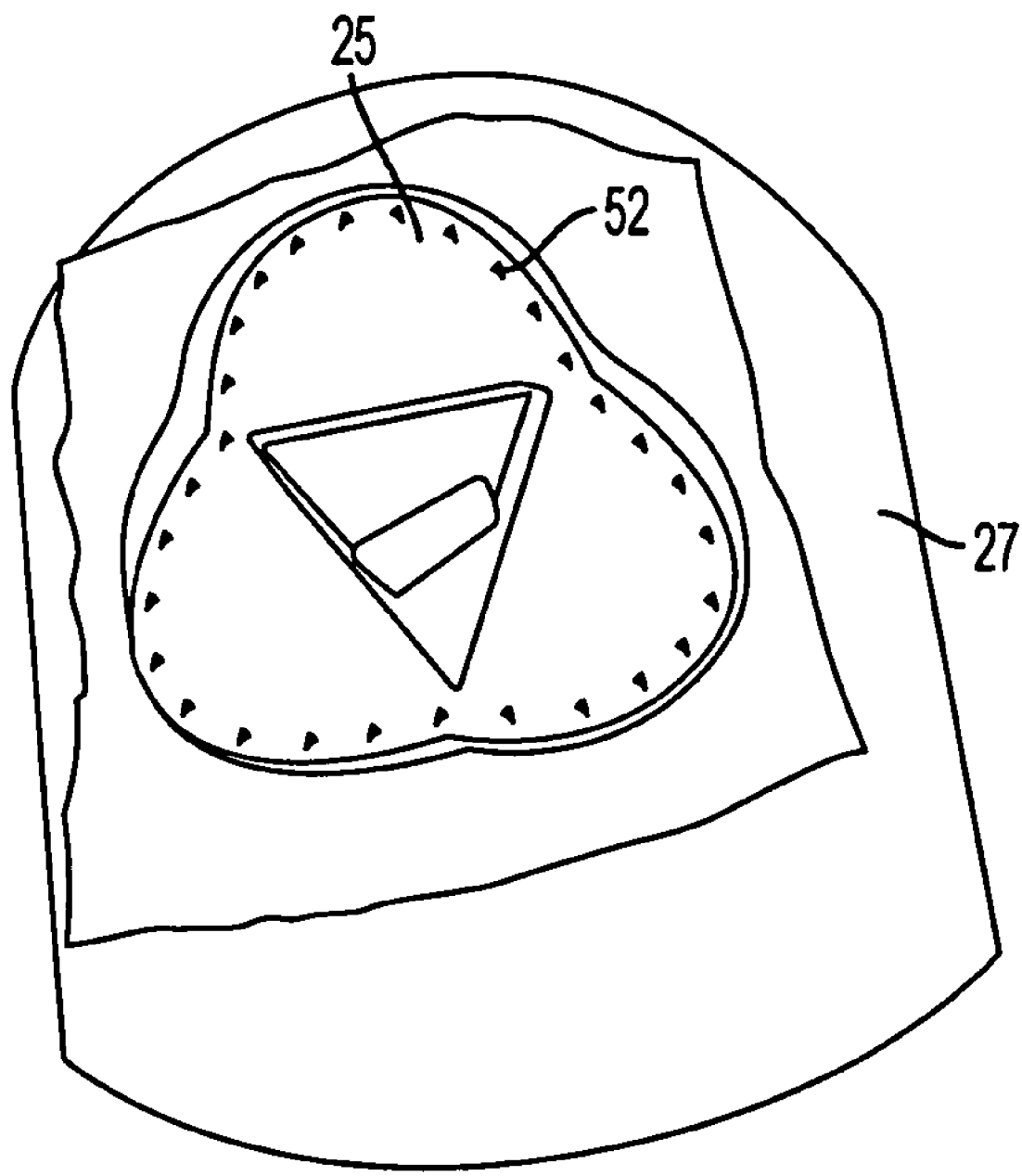
FIG. 12 illustrates a cut piece of tissue on a tissue holding plate.

After the tissue has been cut and the blade retaining member 24 is raised slightly, tissue holding plate 27 can be removed from slot 58 so that the cut tissue pattern can be extracted. FIG. 12 illustrates a cut piece of tissue 25 on tissue holding plate 27. In the illustrated embodiment, the tissue pattern comprises a preferred trefoil shape having a center orifice 19 for use in the repair and/or reconstruction of semilunar heart valves. Barbs 52 preferably extend through the tissue so as to adhere the tissue to stent 50 (FIGS. 6–9). As described in co-pending application Ser. No. 10/898,703, the barbs can be used to attach the valve structure to the wall of a vessel to provide a replacement heart valve.

Thus, the cutting device of the present invention provides a mechanism for quickly and easily cutting a precise tissue pattern. In addition, the cutting device can also quickly attach a stent to the valve repair material. Furthermore, the cutting device cannot readily be re-used so as to avoid the risk of contamination, infection, an ineffective cutting resulting from the re-use of the cutting blade.

Although the invention has been described with reference to a specific embodiment, it should be understood that various changes may be made without departing from the spirit or scope of the invention. For instance, the pattern of the die blade can be modified to cut tissue of various predetermined shapes. The housing could also be any of a variety of shapes. In addition, various pressure mechanisms can be used to force the blade retaining member downward.

Accordingly, the disclosed examples are intended to be illustrative of the scope of the invention and are not intended to be limiting. The scope of the invention is defined as set forth in the appended claims.

I claim:

1. A single-use surgical cutting device for cutting a planar piece of tissue into a predetermined shape, the cutting device comprising:
   a. a housing having one or more side walls, a top, a base, and a hollow interior portion;
   b. a blade retaining member having a top surface and a bottom surface, the blade retaining member being disposed within the housing between the top and base such that top surface and bottom surface of the bade retaining member are substantially parallel to the top and the base of the housing and the blade retaining member can move vertically between the top and base, the bottom surface of the blade retaining member having a blade disposed thereon, the blade defining the predetermined tissue shape;
   c. a pressure mechanism creating potential energy for exerting a downward force on the top surface of the blade retaining member, such that when the blade retaining member is released, the pressure mechanism forces the blade retaining member downward with sufficient force to cut the piece of tissue; and
   d. an actuator configured to release the blade retaining member upon actuation only once without disassembling the housing and resetting the pressure mechanism;
   whereby the piece of tissue can be placed beneath the bottom surface of the blade retaining member on or parallel to the base and the actuating mechanism can be actuated to release the downward force on the blade retaining member to cut the piece of tissue into the desired shape, but the cutting device cannot readily be reused by an operator, wherein the pressure mechanism comprises one or more springs compressed between the top of the housing and the blade retaining member and the actuating mechanism comprises a mechanism for releasing the compressed springs, wherein:
   the top of the housing has a circular center hole;
   the actuator comprises:
      i. a cylindrical shaft passing through the center hole having a top end and a bottom end;
      ii. a knob attached to the top end of the shaft which rests on the top of the housing for rotating the shaft about its axis;
      iii. one or more horizontal projections from the bottom end of the shaft which project from the shaft orthogonal to the axis of the shaft;
   the blade retaining member comprises a center opening having a profile that allows the bottom end of the cylindrical shaft and projections to pass through the blade retaining member only when aligned with the center opening; and
   wherein the cutting device can be placed in a ready position by passing the bottom end of the shaft and projections through the center opening of the blade retaining member, pressing the blade retaining member upward against the top of the housing to compress the springs, rotating the shaft such that the pins are not aligned with the center opening of the blade retaining member so as to retain the blade retaining member against the housing with the springs in a compressed condition; and the cutting device can be actuated from the ready position by turning the knob to a cut position where the projections are aligned with the center opening of the blade retaining member so as to allow the projections and bottom end of the shaft to pass through the center opening of the blade retaining member and release the blade retaining member, allowing the springs to decompress and force the blade retaining member downward.

2. A single-use surgical cutting device for cutting a planar piece of tissue into a predetermined shape, the cutting device comprising:
   a. a housing having one or more side walls, a top, a base, and a hollow interior portion;
   b. a blade retaining member having a top surface and a bottom surface, the blade retaining member being disposed within the housing between the top and base such that top surface and bottom surface of the bade retaining member are substantially parallel to the top and the base of the housing and the blade retaining member can move vertically between the top and base, the bottom surface of the blade retaining member having a blade disposed thereon, the blade defining the predetermined tissue shape;
   c. a pressure mechanism creating potential energy for exerting a downward force on the top surface of the blade retaining member, such that when the blade retaining member is released, the pressure mechanism forces the blade retaining member downward with sufficient force to cut the piece of tissue;
   d. an actuator configured to release the blade retaining member upon actuation only once without disassembling the housing and resetting the pressure mechanism; and
   e. a tissue holding plate;
   whereby the piece of tissue can be placed beneath the bottom surface of the blade retaining member on or parallel to the base and the actuating mechanism can be actuated to release the downward force on the blade retaining member to cut the piece of tissue into the desired shape, but the cutting device cannot readily be reused by an operator,
   wherein the housing comprises a slot in a side wall near the base for receiving the tissue holding plate and retaining it below the blade retaining member during cutting, and
   wherein the tissue holding plate comprises a lower base plate and an upper tissue retaining plate removably configured to be positioned on and attached to the lower base plate, the upper tissue retaining plate having an opening therein for allowing the blades to pass through, whereby the tissue can be held on the tissue holding plate by sandwiching the tissue between the lower base plate and upper tissue retaining plate.

3. The device of claim 2, further comprising retaining tabs on the lower base plate for securing the upper tissue retaining place to the lower base plate.

4. The cutting device of claim 3, further comprising a mechanism for raising the blade retaining member after the tissue has been cut to allow the tissue and holding plate to be removed from the housing.

5. A portable, single-use surgical cutting device for cutting a planar piece of tissue into a trefoil shape optimized for use in the repair or reconstruction of a semilunar heart valve, the cutting device comprising:
   a. a substantially cylindrical, essentially hand-sized housing constructed such that it cannot be easily disassembled by an operator, the housing defining a hollow substantially cylindrical interior, the housing comprising:

i. an upper housing comprising a substantially cylindrical side wall defining a cylindrical interior, the side wall having a upper portion and a lower portion, the side wall having a slot on the lower portion, and a top adjoining the upper portion;
ii. a substantially circular base plate attached to the lower portion of the upper housing;

b. a substantially circular blade retaining member fitting closely inside the hollow cylindrical interior, the blade retaining member having a top surface and a bottom surface, the blade retaining member being disposed within the housing between the top of the upper housing and base plate such that the top surface and bottom surface of the blade retaining member are substantially parallel to the top of the housing and base plate and the blade retaining member can move vertically between the top of the housing and the base plate, the bottom surface of the blade retaining member having a blade disposed thereon, the blade defining a trefoil shape optimized for use in the repair or reconstruction of a semilunar heart valve;

c. one or more springs compressed between the top of the housing and the blade retaining member creating potential energy for exerting a downward force on the top surface of the blade retaining member, such that when the blade retaining member is released, the springs force the blade retaining member downward with sufficient force to cut the piece of tissue; and d. an actuator configured to releasably retain the blade retaining member in a ready position with the springs compressed between the top of the housing and the blade retaining member and release the blade retaining member upon actuation only once without disassembling the housing and resetting the pressure mechanism;

e. a tissue holding plate for receiving and retaining the piece of tissue under the blade retaining member during cutting, the tissue holding plate sized to be inserted into the slot in the side wall of the housing;

f. a mechanism for raising the blade retaining member after cutting to allow the tissue holding plate to be removed from the slot, whereby the cut tissue can be removed from the device;

whereby the piece of tissue can be placed beneath the bottom surface of the blade retaining member on or parallel to the base plate and the actuating mechanism can be actuated to release the downward force on the blade retaining member to cut the piece of tissue into the desired trefoil shape, but the cutting device cannot readily be reset for reuse by the operator.

6. The cutting device of claim 5, wherein:
a. the housing has a circular center hole;
b. the actuator comprises:
i. a cylindrical shaft passing through the center hole having a top end and a bottom end;
ii. a knob attached to the top end of the shaft which rests on the top of the housing for rotating the shaft about its axis;
iii. one or more horizontal projections from the bottom end of the shaft which project from the shaft orthogonal to the axis of the shaft;
c. the blade retaining member comprises a center opening having a profile that allows the bottom end of the cylindrical shaft and projections to pass through the blade retaining member only when aligned with the center opening;

wherein the cutting device can be placed in a ready position by passing the bottom end of the shaft and projections through the center opening of the blade retaining member, pressing the blade retaining member upward against the top surface of the housing to compress the springs, rotating the shaft such that the pins are not aligned with the center opening of the blade retaining member so as to retain the blade retaining member against the housing with the springs in a compressed condition; and the cutting device can be actuated from the ready position by turning the knob to a cut position where the projections are aligned with the center opening of the blade retaining member so as to allow the projections and bottom end of the shaft to pass through the center opening of the blade retaining member and release the blade retaining member, allowing the springs to decompress and force the blade retaining member downward.

7. The device of claim 5, wherein the tissue holding plate comprises a top surface having a trefoil-shaped slot for receiving a trefoil-shaped stent to be attached to the tissue, such that, when inserted into the slot, the stent is flush with the top surface of the tissue holding plate.

8. The device of claim 5, wherein the tissue holding plate comprises a lower base plate and an upper tissue retaining plate removably configured to be positioned on and attached to the lower base plate, the upper tissue retaining plate having an opening therein for allowing the blades to pass through, whereby the tissue can be held on the tissue holding plate by sandwiching the tissue between the lower base plate and upper tissue retaining plate.

9. The device of claim 5, further comprising retaining tabs on the lower base plate for securing the upper tissue retaining place to the lower base plate.

* * * * *